United States Patent
Tuunanen

(10) Patent No.: US 7,504,641 B2
(45) Date of Patent: Mar. 17, 2009

(54) POLARISATION FLUOROMETER

(75) Inventor: Jukka Tuunanen, Helsinki (FI)

(73) Assignee: Thermo Electron, Vantaa (FI)

( * ) Notice: Subject to any disclaimer, the term of this patent is extended or adjusted under 35 U.S.C. 154(b) by 18 days.

(21) Appl. No.: 10/571,536

(22) PCT Filed: Sep. 10, 2004

(86) PCT No.: PCT/FI2004/000524

§ 371 (c)(1),
(2), (4) Date: Jan. 16, 2007

(87) PCT Pub. No.: WO2005/024402

PCT Pub. Date: Mar. 17, 2005

(65) Prior Publication Data

US 2007/0200073 A1    Aug. 30, 2007

(30) Foreign Application Priority Data

Sep. 10, 2003    (FI)    ................................ 20031294

(51) Int. Cl.
*G01N 21/64* (2006.01)
(52) U.S. Cl. .................... 250/458.1; 250/225; 356/436; 356/435; 356/364
(58) Field of Classification Search .................. None
See application file for complete search history.

(56) References Cited

U.S. PATENT DOCUMENTS

| | | |
|---|---|---|
| 4,074,939 A | 2/1978 | Rabl et al. |
| 4,521,111 A | 6/1985 | Paulson, Jr. et al. |
| 4,622,468 A * | 11/1986 | Stefanski et al. ......... 250/458.1 |
| 6,297,018 B1 | 10/2001 | French et al. |

FOREIGN PATENT DOCUMENTS

| | | |
|---|---|---|
| WO | 91/07652 | 5/1991 |
| WO | 97/11354 | 3/1997 |
| WO | WO 03/016979 | 2/2003 |

OTHER PUBLICATIONS

Driggers, R., "Illumination Optics", Encyclopedia of Optical Engineering, CRC Press, 2003, p. 1234.*
"Simultaneous Measurement of Circular Dichroism and Fluorescence Polarization Anisotropy," John C. Sutherland (pp. 126-136) Clinical Diagnostic Systems: Technologies and Instrumentation Proceedings of SPIE vol. 4625 (2002) © 2002 SPIE.

* cited by examiner

*Primary Examiner*—David P Porta
*Assistant Examiner*—Yara B Green
(74) *Attorney, Agent, or Firm*—Oblon, Spivak, McClelland, Maier & Neustadt, P.C.

(57) ABSTRACT

A polarization fluorometer and a method for calibrating such a fluorometer. The fluorometer includes an excitation channel with an excitation polarizer for generating light polarized in a first plane or in a second plane to be conducted as a excitation light to a sample, an emission channel for conducting emission light from the sample, in which emission channel there is an emission polarization filter, an excitation detector, to which light polarized by the excitation polarizer can be conducted from the excitation channel, and a reference detector, to which light polarized by the excitation polarizer can be conducted from the excitation channel before being conducted to the sample or to the excitation detector. The reference detector can be calibrated by the excitation detector so that correction measurements can be carried out in real time during sample measurement. The fluorometer can be used especially for fluorescence spectra measurements.

14 Claims, 3 Drawing Sheets

POLARISATION FLUOROMETER

FIELD OF TECHNOLOGY

Figure 1:
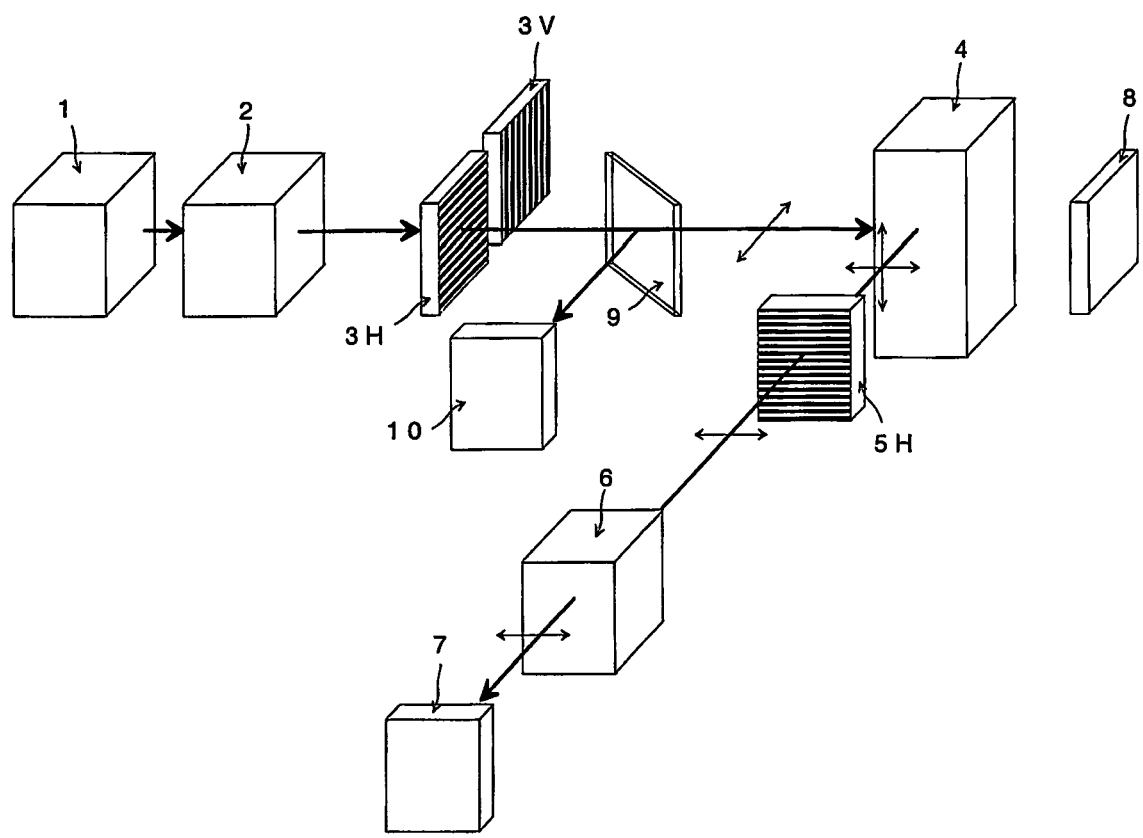

The invention relates to a polarisation fluorometer and is directed to the calibration of the fluorometer. The invention is applicable to analysers for examining the chemical properties of samples by means of polarisation fluorometry. Such studies are conducted in biotechnology and clinical chemistry laboratories in particular.

TECHNOLOGICAL BACKGROUND

In fluorometry, excitation light on a given wavelength is directed to a sample. Illumination generates fluorescence in any fluorophore present in the sample, thus generating emission light having a longer wavelength.

If the excitation light is polarised, it will act in the fluorophore molecules settled correctly relative to the excitation light polarisation, and the emission light is polarised as well. The emission polarisation angle is specific for the fluorophore and dependent on the wavelength.

An emission may be depolarised for different reasons. Depolarisation is caused by the molecule state shifting between excitation and emission. The typical time difference is about 10 nanoseconds. Depolarisation can be used in different ways, e.g. for monitoring chemical reactions. A main cause of depolarisation is circular oscillation of a molecule. The extent of circular motion depends, among other things, on the shape and size of the molecule and on the viscosity of the medium. Depolarisation will thus be affected by the average circular motion of the molecules of the substance during the time difference between excitation and emission. If a fluorescent molecule is associated with another molecule, this will result in retarded circular motion of the fluorophore and increased polarisation of the emission.

In biotechnological applications in particular, a fluorescent fluorophore has frequently been associated with a molecule adhering specifically to identifiable molecules. An increased molecule size causes retarded circular motion of the molecule, the fluorophore thus better retaining the original polarisation level. A measurement of the polarisation thus allows direct and rapid measurement of such a specific reaction. A spectral polarisation measurement may also provide important information about the sample, involving measurement of the polarisation of the sample at different excitation or emission wavelengths.

Polarisation fluorescence is particularly suitable in the analysis of large sample quantities owing to the rapid method and the reliable measuring process.

Polarisation is measured by means of a fluorometer comprising a polarisation filter both in the excitation and the emission channel.

Two measurements are required for calculating polarisation:
1. An excitation polarisation filter and an emission polarisation filter in alignment
2. An excitation polarisation filter and an emission polarisation filter at a mutual angle of 90 degrees The polarisation P is derived from the formula:

$$P=(I_{\parallel}-I_T)/(I_{\parallel}+I_T) \quad \text{formula (1)}$$

in which
$I_{\parallel}$: emission intensity with parallel filters
$I_T$: emission intensity with crossed filters The polarisation quantity is also described with the term anisotropy r:

$$r=(I_{\parallel}-I_T)/(I_{\parallel}+2I_T) \quad \text{formula (2)}$$

P and r can hence be calculated from each other:

$$P(r)=3r/(2+r) \quad \text{formula (1a)}$$

Polarisation fluorometers normally use so-called L geometry, in which emission light is measured at a 90-degree angle to the excitation light. This reduces efficiently the access of excitation light to the emission detector. In the usual configuration, the excitation channel uses a stationary polarisation filter and the emission filter uses a replaceable polarisation filter, but this configuration can also be inversed.

Assumedly, the excitation channel comprises a stationary polarisation filter whose polarisation plane is X. The emission of the sample is measured with this polarisation, yielding $I_{XX}$. A second measurement is performed with the emission polarisation turned by 90 degrees (plane Y), yielding $I_{XY}$. In the ideal case, the polarisation can be calculated directly from the emission measurement results $I_{XX}$ and $I_{XY}$:

$$P=(I_{XX}-I_{XY})/(I_{XX}+I_{XY}) \quad \text{formula (3)}$$

However, the transmission level of the signal from the emission channel and the transmittance of the emission polarisation filter can vary in intensity on different polarisation planes. This is why a calibration factor is necessary for compensating the difference between the measurement sensitivities of different polarisations. The calibration factor is called the G factor. The polarisation thus compensated is derived from the formula:

$$P=(I_{XX}-GI_{XY})/(I_{XX}+GI_{XY}) \quad \text{formula (4)}$$

With the sensitivities of the emission measurement on different polarisation planes being $S_Y$ and $S_X$, the G factor is their mutual relationship:

$$G=S_X/S_Y \quad \text{formula (5)}$$

The G factor can be determined if a replaceable polarisation filter is also available on the excitation side. G is calculated by measuring the polarisation of the sample with the two excitation polarisations. Nevertheless, this manner of measuring involves numerous problems:

1. A complex design; a dual polarisation filter, requiring the filter to be positioned at an angle of exactly 90 degrees.
2. The measurement consists of four measurements and is hence slow. The G factor can be measured in advance on a suitably representative sample on a high signal level. This is awkward if the measurement is conducted on a sample whose polarisation is unknown. Replacement of polarisation filters is also a relatively slow operation considering the actual measurement period.
3. Noise; the noise of P consists of all of the four polarisation measurement components. The measurement requires a sample with adequate fluorescence for the noise factors to be minimised.

Because of the problems mentioned above, the G factor is in fact measured in most concrete cases by using a reference sample whose polarisation P is known. G can then be derived from the term of P (formula (4)). Fluoresceine, for example, is such a reference substance. This method also involves problems:

1. Maintaining the solution for any incidental measurements; fluoresceine, for instance, is apt only for applications using fluoresceine as a fluorophore.
2. Spectral polarisation measurements as a function of the excitation wavelength and the emission wavelength (P(λ))

are difficult to carry out. It is necessary to know exactly both the P($\lambda_{excitation}$) and the P($\lambda_{emission}$) spectrum of the reference substance.

WO 91/07652 proposes optics and method for measuring source corrected fluorescence polarisation. In this arrangement the fluorometer relies upon a reference photodetector for monitoring the intensity of light source and for correcting the measured fluorescent intensities. In the excitation channel there is an adjustable polariser, and in the emission channel a fixed one. Only two measurements are needed for the correction: one at each position of the excitation polariser. Correction measurements may be performed with a blank cuvette or with no cuvette.

SUMMARY OF THE INVENTION

A polarisation fluorometer, a method for calibrating a polarisation fluorometer, and a use of a fluorometer as defined in the independent claims have now been invented. The other claims define some of embodiments of the invention.

In accordance with the invention, the emission channel uses a stationary polarisation filter and the excitation channel uses a replaceable polarisation filter. Calibration of the device merely requires measurement of the excitation intensity on the two polarisation planes. No sample is needed for this, and the measurement can be performed directly on the path of the excitation light. Thus a device with L geometry can comprise a special excitation detector (especially free from polarisation) suitable specifically for measuring excitation intensity. There is also a reference detector, to which polarised light can be conducted from the excitation channel, especially via a beam splitter, before being conducted to the sample or to the excitation detector. This reference detector can be calibrated on the basis of the excitation detector so that measuring sensitivities of the fluorometer on the polarisation planes can be calculated also without conducting light to the excitation detector. Thereby e.g. fluorescence spectra can be correctly measured.

DRAWINGS

Figure 2:
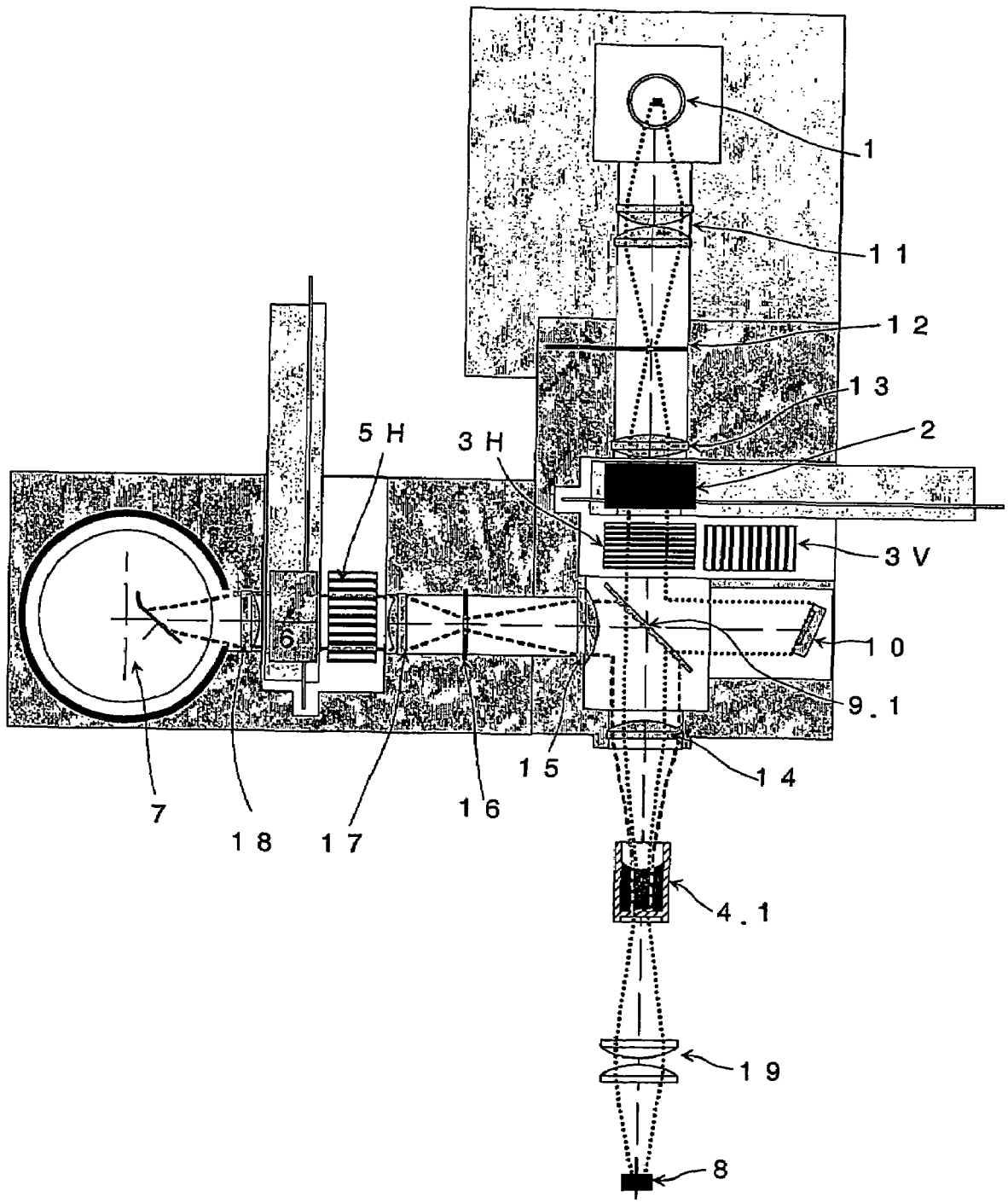
Figure 3:
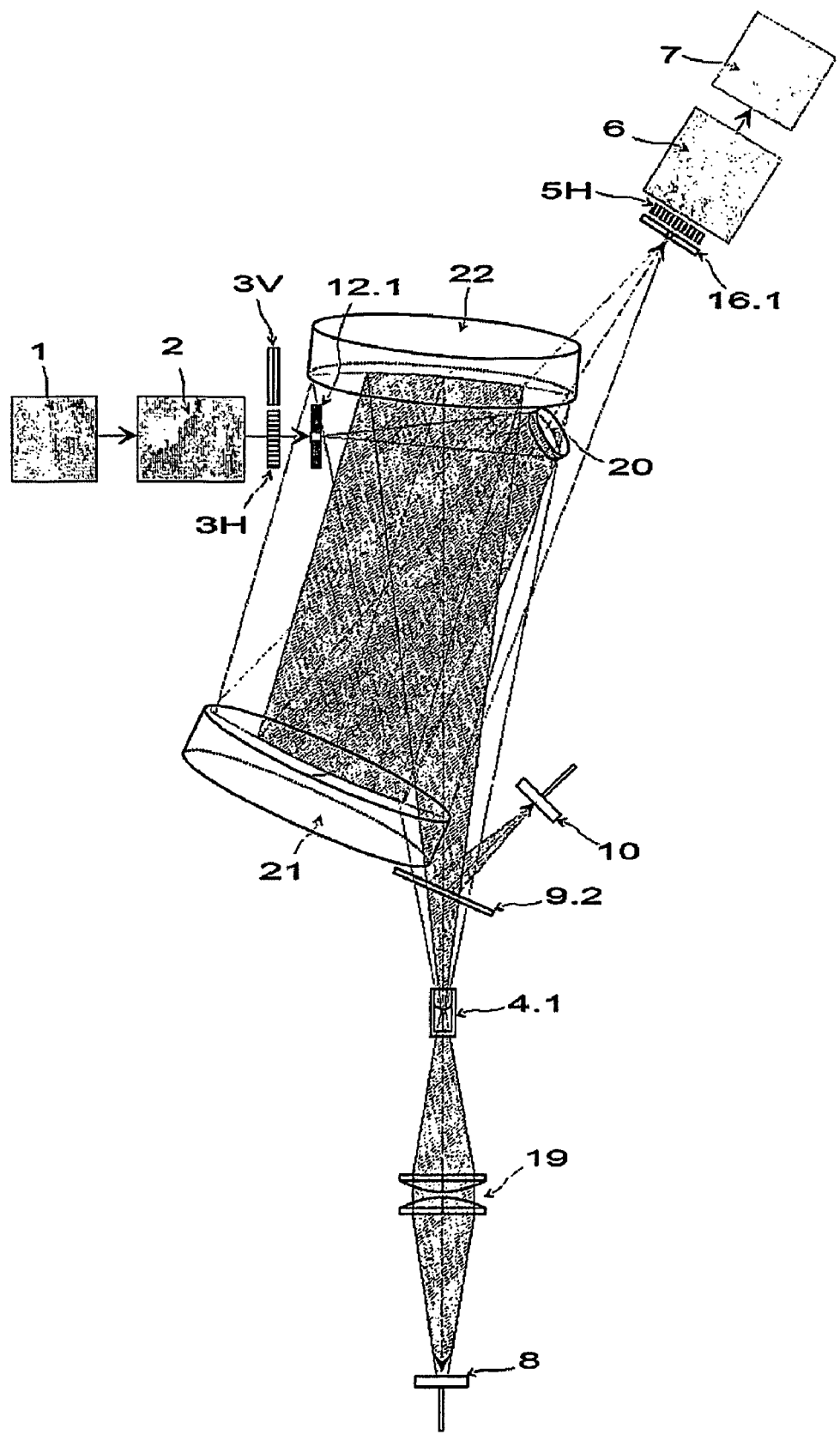

The accompanying drawings form a part of the written disclosure of the invention and relate to the following detailed description of the invention. In the drawings FIG. 1 shows a polarisation fluorometer measurement principle with L geometry FIG. 2 shows a polarisation fluorometer carried out with lens optics and intended for measuring wells on a matrix plate, and FIG. 3 shows a polarisation fluorometer carried out with mirror optics for measuring wells on a matrix plate.

DETAILED DESCRIPTION OF THE INVENTION

In accordance with the invention, the emission channel uses a stationary polarisation filter and the excitation channel uses a replaceable filter. When the polarisation plane of the emission channel is marked with X and the polarisation plane perpendicular to this is marked with Y, the polarisation P is derived from the formula:

$$P=(I_{XX}-GI_{YX})/(I_{XX}+GI_{YX}) \quad \text{formula (6)}$$

$$G=E_X/E_Y \quad \text{formula (7)}$$

in which
$I_{XX}$=emission intensity with the excitation plane X
$I_{YX}$=emission intensity with the excitation plane Y
$E_X$=excitation intensity on plane X
$E_Y$=excitation intensity on plane Y Combining formulas (6) and (7) yields $$P=(I_{XX}/E_X-I_{YX}/E_y)/(I_{XX}/E_X+I_{YX}/E_y) \quad \text{formula (8)}$$

Hence the determination of the G factor only requires two measurements. The components of the G factor in this case having been formed before the sample, measurements for determining the G factor can be carried out in the absence of the sample using an excitation detector, which is placed on the path of the excitation beam, in other words, without conducting light through the emission channel.

The excitation G factor measurement in this way yields significant advantages, among other things:

1. The measurement is fully independent of the sample. The measurement is preferably performed without any sample and also without using any sample vessel.
2. The measurement is rapid, considering that the actual determination requires only two measurements. Owing to the calibrated reference channel, the determination requires only two measurements.
3. No additional components are required if photometric measurement has already been provided in the device, i.e. it allows simultaneously for photometric measurement.
4. With low sample concentrations the noise P of the polarisation is low, because the result only consists of two low-level measurement result components. The two other factors required for calculating the G factor of the polarisation are practically noiseless owing to the high signal level.

With the use of separate excitation polarisation filters, the filter can be replaced with a linear movement, allowing easy high-precision positioning. One could optionally use one single filter, which is turned between measurements.

The light source may comprise e.g. an incandescent bulb (e.g. halogen lamp), which generates a wide uniform spectrum and is thus suitable for versatile measurements. A deuterium lamp is also usable, especially when a strong illuminating effect in the ultra-violet range is desired. A xenon flashlight is nevertheless a particularly suitable light source. This light source allows a very large excitation wavelength range to be covered. The flashlight source generates short light pulses of very high intensity. The use of a flashlight lamp is efficient, because the lamp is in operation at the moment of measurement alone.

For the determination of the G factor, it is possible to use an excitation detector that is specifically free from polarisation and optimally suitable precisely for measuring excitation intensity. The detector may be located e.g. after the sample area, allowing the detector to be in fixed position without interfering with the positioning of the sample. The excitation detector may be e.g. a silicon photodetector or a photo multiplier tube (PMT). A silicon photodetector located perpendicularly to the excitation light to be measured is a particularly suitable detector. Lens or mirror optics, for instance, may be provided in front of the detector with a view to enlarging the effective area of the detector. The excitation detector measuring the G factor may also be located before the sample vessel.

In accordance with the invention, there is also a second detector, called reference detector, and this reference detector is located before the said excitation detector and also before the sample. The reference detector can be used also when a sample placed in the fluorometer prevents the use of the excitation detector. A part of the polarised light is conducted to the reference detector preferably via a suitable means. Such means cause polarisation both in the transmitted light beam and in the reflected light beam. These phenomena depend on the wavelength. For this reason, a measurement performed through such a means will be inaccurate unless it is separately calibrated. This calibration can be done before placing the sample into the fluorometer by means of the excitation detector. When the reference detector has been calibrated, it can be used for measuring the G factor in real time during the sample measurement, also when there is sample on the light path of the excitation detedtor. Thereby the drifts of electric and optic components can be very reliably taken into count in the calculations. This is a significant advantage especially when fluoresence sprectra are measured. In such measurements it takes typically about 10 minutes to measure at each polarisation plane.

The means for conducting a part of the light may be e.g. a glass plate, semitransparent mirror, a mirror smaller than the area of the excitation channel, or an optical fiber The excitation detector allows calibration of the reference detector to make it measure correctly the polarisation characteristics of the excitation channel. The reference detector as such does not provide exact measurements of the polarisation characteristics of the excitation channel especially because of the polarisation behaviour of the means for conducting part of the light. However, such means have stable polarisation behaviour, so that, after a measurement by means of a photometric detector and a reference detector, the reference detector can be calibrated with a view to the polarisation measurement of the excitation channel. This makes the measuring process even more rapid, since a calibrating run of the G factor is not required before the measurement. Nevertheless, a periodic calibrating run will be necessary in cases where a high-precision G factor is required.

If the excitation detector gives at the vertical and horizontal planes signals $F_V$ and $F_H$ and the reference detector at the same time signals $R_v$ and $R_H$, and if the actual signals obtained by the reference detector during the sample measurements are $R_{va}$ and $R_{Ha}$, the corrected G factor $G_{corr}$ is $$G_{corr}=k*G=k*R_X/R_Y \qquad \text{formula (A)}$$

$$k=(F_{XC}/F_{YC})*(R_{YC}/R_{XC}) \qquad \text{formula (B)}$$

$$P=(I_{XX}-G_{corr}I_{YX})/(I_{XX}+G_{corr}I_{YX}) \qquad \text{formula (C)}$$

in which
$R_{XC}$=reference channel intensity in calibration phase on plane X
$R_{YC}$=reference channel intensity in calibration phase on plane Y
$F_{XC}$=photodetector intensity in calibration phase on plane X
$F_{YC}$=photodetector intensity in calibration phase on plane Y
$R_X$=reference channel intensity in measurement phase on plane X
$R_Y$=reference channel intensity in measurement phase on plane Y
$I_{XX}$=emission intensity with the excitation plane X
$I_{YX}$=emission intensity with the excitation plane Y.

Combining formulas (A) and (B) and (C) yields $$P=(I_{XX}/E_X-kI_{YX}/E_Y)/(I_{XX}/E_X+kI_{YX}/E_Y) \qquad \text{formula (D)}$$

$$k=(F_{XC}/F_{YC})*(R_{YC}/R_{XC}) \qquad \text{formula (E)}$$

Formula (E) contains information only form calibration phase and formula (D) contains information only from measurement phase.

Unless the intensity of the light source remains sufficiently constant over the various measurement stages, also the intensity of the light source must be measured before the sample. In the practice the intensity measurement is necessary. This is especially the case when xenon flashlight illumination is used. Xenon flashlight has instability of the order of 0.5 . . . 1%. In the practice, a reference measurement will be required in each measuring step.

In the fluorometer in accordance with the invention, the reference intensity measurement can be performed using the reference detector used already for the measurement of the G factor. The fluctuating level of the light source is taken into account by means of a signal from the reference detector. Because in P-formula each emission intensity ($I_{XX}$, $I_{YX}$) value is measured with corresponding excitation value ($E_X$, $E_Y$), the flash fluctuation is automatically cancelled. No additional signal processing is needed.

For the emission to be exactly measured, both the excitation and the emission wavelengths should be carefully filtered. The choice of emission wavelength shall prevent the excitation light from proceeding directly to the emission measurement detector.

The wavelength is selected in the excitation and emission channels by means of a monochromator. The monochromator may be based on interference, especially on thin membranes, or on natural transmittance of the substance. The monochromator may be e.g. a grating monochromator or a colour filter. The monochromator configurations may comprise several stages for increased filtering effect. The term monochromator may hence denote an apparatus comprising 1 . . . n identical or different monochromator elements.

Lens or mirror optics can be used for light conduction.

A photomultiplier tube is frequently used as an emission light measurement detector, because the optical signals to be measured are very small, thus requiring high measuring sensitivity. Silicon photodetectors are also used. Such detectors have the benefit of excellent stability.

The polarisation filter of the emission channel may also be replaceable in accordance with the wavelength range to be used. Often one polarisation filter covers the UV range, another the visible range, and a third the near IR range.

In many cases, a fluorometric measurement and measurement of the transmission of a sample relate to measurements of samples in the same area. It is advantageous for the user that the same apparatus performs both fluorometric measurements and photometric measurements of optic density, because a combined apparatus is more economical than two separate ones. Crowded laboratories also favour the use of combined equipment.

The samples are usually treated on plates, where sample vessels, i.e. wells are located in a bi-dimensional matrix. There are typically 6 . . . 1536 wells, while the plate area is quite constant. In most cases, there are 96 or 384 wells on the plate. The outer dimensions and number of wells may vary in special applications.

With the wells forming a very narrow matrix on the plate, L measurement geometry is not applicable. Free measuring directions are allowed either from the upper side or the lower side of the well. Due to problems of background fluorescence, measurement through the bottom window is preferably avoided in fluorometry. In addition, polystyrene, which is the most frequently used material in the plates, is inapt for polarisation measurements through the bottom, because it interferes polarisation planes randomly.

An excitation beam can be given a conically tapered shape in the well for the size of the excitation beam to be smaller than the well diameter. This achieves good channel separation between the wells and the positioning tolerances of the well will impair the measurement results as little as possible.

Consequently, a replaceable excitation polarisation filter is used: one may choose either a V or an H filter, or the filter can be eliminated from the measurement of fluorescence intensity. The polarisation filters may be optimally changed in accordance with the wave length. The polarisation filter may also be a rotatable one. A rotating filter allows accurate measurement of the angular value of the polarisation maximum when the polarisation of the substance to be determined has a characteristic angle of rotation, with which the molecule oscillation subsequently interferes. A rotating filter is particularly suitable for measuring viscous samples.

Hence the preferred measuring direction is from the upper side of the well: both excitation lighting and emission measurement are performed from above the well. With both excitation and emission using the same path, they are separated from each other by a beam splitter. One such means is disclosed in WO 97/11354, in which fluorometric optics has been carried out with lens optics. By incorporating polarisation filters in the excitation and emission channels, the G factor measurement described above can be performed with the aid of a photodetector placed under the well. At the same time, this provides the option of photometric measurement.

The beam splitter may be especially a semitransparent mirror, in particular such that is divided into mirror surfaces by sectors. Owing to the low diffraction effect, such a window will not interfere with the quality of the excitation measurement beam. The mirror may also be divided e.g. into concentric circles or more advantageously into ellipses. If the excitation light proceeds linearly, the mirror has a hole in the centre and its border area is reflective. In this case, the excitation light will have a narrow solid angle compared to the emission light path. This is advantageous for photometry, considering that light transmission through a narrow well is difficult in photometry. Photometric excitation light will have to penetrate through a sharply concave liquid surface (usually a detergent is employed for stabilising the surface to maximum concavity), and for this reason the excitation light should have a very narrow solid angle and should be focused exactly to the correct height. The mirror may also be dichroic. Such a mirror reflects different wavelengths in different manners. Since the excitation wavelength is smaller than the emission wavelength, the wavelength characteristics of the mirror can be adapted so as to yield optimal overall efficiency. A dichroic mirror involves the problem of being practicable on only one pair of excitation-emission wavelengths.

The beam splitter separating excitation and emission may also serve as a beam splitter for the excitation light to be separated to the reference detector, so that the construction will thus be straightforward.

Measurement of the plate can also be carried out by means of mirror optics. The use of two spherical mirrors connected in sequence is especially preferred. However, a spherical mirror generates strong astigmatism and thus degrades imaging characteristics in the measurement of narrow wells. If, however, mirrors connected in sequence have turning planes at an angle of 90 degrees, the astigmatism will be compensated. In other words, the error is made twice, but the astigmatism error of the second mirror compensates the astigmatism error of the first mirror and the imaging result will be good with a view to fluorometric and photometric measurement. This principle has been described in detail in WO 03/016979. The mirrors are spherical and concave. Such mirrors are accurate and have lower production costs compared to aspheric mirrors. Mirror optics can be carried out also with the aid of substantially more expensive aspheric mirrors, allowing the use of e.g. one single mirror for generating a conical and accurate excitation light beam.

In mirror optics, the beam splitter may be any one of those used in lens optics as mentioned above.

Mirror optics has the advantage of being independent of the wavelength.

When mirror optics employs a grating monochromator as the excitation monochromator, the output slit of the grating to the well is imaged. Excitation polarisation filters are preferably placed in the vicinity of the slit. The excitation polarisation filters are placed after the monochromator, since monochromators cause depolarisation (i.e. degeneration of polarisation). The emission polarisation filter is preferably placed in the vicinity of the input slit of the emission monochromator. The excitation and emission light beams can be separated from each other along their common optical measuring axis by means of a small (e.g. circular or elliptic) planar mirror. The emission light will return from the well to the optics and pass by this mirror. In addition, a beam splitter may be provided for the reference channel just above the well. This beam splitter is e.g. a glass plate, especially a silica plate (synthetic quartz). A silica plate typically reflects a maximum of about 10%, and hence there will be relatively small signal loss. The glass plate simultaneously protects the optics against vapours from the wells.

The excitation detector is located on the other side of the well. A lens system may be provided in front of the detector (e.g. two plano-convex lenses), for the excitation light enlarged by the liquid surface in the well to be better focussed on the surface of the photodetector. Lens optics can be replaced with mirror optics by using e.g. two concave mirrors in the same manner as in excitation optics.

The excitation light source and monochromator, and also the emission monochromator and detector, may require a relatively large space. For a smaller analyser size, the use of fibre optics may be convenient, even though there would occur signal loss in that case. The analyser may comprise e.g. three modules: an excitation module, a measurement optics module and an emission module, with fibre optics used for conducting light between these.

EXAMPLES

Examples of different embodiments of the invention are given below. The examples use a horizontal polarisation plane in the emission channel, however, similar arrangements can naturally be carried out e.g. by means of vertical emission polarisation. The relative mutual position of the polarisation filters of the excitation channel and the emission channel is essential in this case.

In the fluorometric measurement illustrated in FIG. 1, the excitation light from light source 1 is conducted to excitation monochromator 2 and through the excitation polarisation filter $3_H$ or $3_v$ to the sample vessel 4. The emission light generated in the sample vessel is conducted in a direction perpendicular to the excitation light through the emission polarisation filter $5_H$ and the emission monochromator 6. The emission light thus generated is conducted to the detector 7. The emission polarisation filter is thus stationary, while the excitation filter is replaceable.

For determination of the G factor, a detector 8 is provided on the path of the excitation light, behind the sample vessel 4, perpendicular to the light. It may be a silicon photodetector in particular.

For a simple G factor determination, the sample vessel is removed and the excitation intensity is measured in the two excitation filters $3_H$ and $3_v$. Then the G factor is derived from the formula 7 above.

With the use of separate excitation filters $3_H$ and $3_v$, the filter can be replaced with a linear movement, allowing ease of accurate orientation. Optionally, one could use one single filter, which is turned between measurements.

The excitation channel also comprises, after the polarisation filter $3_H$ (or $3_V$), a beam splitter 9, through which light is conducted to a reference detector 10. By means of this reference detector it is possible to determine the G factor in real time also when the sample is in its place. Then the G factor is derived according to formula A above.

A signal from the reference detector allows also for the fluctuating level of the light source to be taken into account.

When the polarisation filters $3_H$ and $3_V$ of the excitation channel are removed, a photometric measurement can be performed using the detector 8. This allows use of the apparatus as combined equipment without any supplementary components.

In FIG. 2, the polarisation fluorometer has a light source 1, from which excitation light is condensed by means of a lens system 11 to an excitation aperture 12. The excitation light from the excitation aperture is collimated with a lens system 13, and the collimated light is conducted through a monochromator 2 (wavelength filter) and a horizontal or vertical polarisation filter $3_H$ or $3_V$ to a semitransparent mirror 9.1.

The light having passed through the mirror 9.1 is converged by means of a focussing lens system 14 to a sample well 4.1 located below. In this manner, a luminous spot is obtained within a defined spatial area in the sample in the well.

The portion of the excitation light reflected from the mirror 9.1 is conducted to a reference detector 10. A representative sample of the excitation light is obtained from the mirror. With half of the light used for excitation, the other half can be utilised in the determination of the excitation amplitude. A parallel light beam can be directed to a detector having a large area, or using a converging lens, to a smaller detector.

The emission light emanating for measurement from the light spot on the sample in the well 4.1 passes through a focussing lens system 14 to the lower surface of the mirror 9.1. The portion reflected from this is used for forming an image of the spot with the aid of a converging lens system 15 in an emission aperture 16. From the aperture, the emission light is conducted through a collimating lens system 17, an emission polarisation filter $5_H$, an monochromator 6 (wavelength filter) and a condenser lens system 18 to the detector 7 (photomultiplier tube).

For through measurement, a through-measurement lens system 19 (e.g. two plano-convex lenses) and a detector 8 (e.g. e silicon photodetector) are provided under the well 4.1. This allows the calibration of the invention described above (without a well) or e.g. a photometric measurement to be performed.

The excitation beam has been shaped by lens optics with a conically tapered shape in the well 4.1 in order to obtain good channel separation between the wells and to avoid any detrimental effect of the positioning tolerances of the well on the measurement results.

The excitation filter is replaceable: one can choose either a vertical $3_V$ or a horizontal filter $3_H$, or the filter can be eliminated altogether in the measurement of fluorescence intensity.

A semitransparent mirror 9.1 may be a window divided into mirror surfaces by sectors. Such a window does not interfere with the quality of the excitation-measuring beam owing to its low diffraction effect.

In the fluorometer of FIG. 3, excitation light from a light source 1 is conducted through a monochromator 2 (grating monochromator) and an excitation polarisation filter $3_H$ and $3_V$ perpendicularly to an excitation aperture 12.1 in the wall of the casing as a dot like object. From the excitation aperture 12.1 the light beam is reflected with a small-sized planar mirror 20 to a first concave mirror 21 so that a parallel light beam is emitted to a second identical concave mirror 22, whose plane of inclination is at an angle of 90 degrees to the plane of inclination of the first mirror. In this arrangement, astigmatism is compensated and the second concave mirror forms a dot like image through a glass window 9.2 provided at the bottom of the casing in a measurement well 4.1 located below. The glass window 9.2 is slightly tilted relative to the light path. A portion of the excitation light is reflected from the window surface to a reference detector 10. The reference detector is located in the image plane formed by the optics, as is the measurement well. The reference detector monitors variations in the intensity of the light beam, and the variations are taken into account in the calculation of intensities. Since the light beam is converging towards the well 4.1, the light beam incident on the reference detector is converged accordingly. With the window reflection being about 10%, the overall signal loss will be about 20%. This does not decrease the sensitivity of the apparatus substantially. To avoid any background fluorescence, the window can be given minimum thickness. The window also provides protection for the measurement optics, the sample well being located in a closed space, from where humidity, or other harmful gases or vapours have no access to the interior of the optics. The window material is preferably silica. The window is preferably placed on a level sufficiently high above the measurement well to prevent splashes from any dosing devices to reach the window surface.

The emission light generated in the measurement well 4.1 proceeds through the second mirror 22 to the first mirror 21 and from there towards the planar mirror 20. Part of the emission light passes by the mirror on its outside, forming a dot like image with corrected astigmatism perpendicularly to an emission aperture 16.1 on the surface of the casing. Hence the planar mirror 20 has the function of separating excitation light from emission light. For maximum efficiency the division ratio is preferably about 50%:50%.

From the emission aperture 16.1, the emission light is conducted through an emission polarisation filter $5_H$ and an emission monochromator 6 (grating monochromator) to a detector 7.

For through measurement, a through measurement lens system 19 (e.g. two plano-convex lenses) and a detector 8 (e.g. a silicon photodetector) are provided under the well 4.1. This allows the calibration of the invention (without a well) or e.g. a photometric measurement to be carried out.

The invention claimed is:

1. A polarisation fluorometer comprising:
   an excitation channel by which polarised excitation light is conducted to a sample, the excitation channel including an excitation polariser configured to generate light polarized in a first plane or excitation light polarised in a second plane to be conducted as an excitation light to the sample;
   an emission channel configured to conduct emission light from the sample, the emission channel including an emission polarisation filter and an emission detector;
   an excitation detector to which light polarized by the excitation polariser is conducted from the excitation channel, and
   a reference detector to which light polarised by the excitation polariser is conducted from the excitation channel before being conducted to the sample or to the excitation detector.

2. A fluorometer as defined in claim 1, wherein the second plane is at an angle of 90 degrees to the first plane.

3. A fluorometer as defined in claim 1, wherein the excitation detector is a detector free from polarisation.

4. A fluorometer as defined in claim 1, further comprising, in front of the excitation detector, an optic system configured to increase an effective area of the excitation detector.

5. A fluorometer as defined in claim 1, further comprising, in the excitation channel, means for conducting a part of the polarised light from the excitation channel to the reference detector and a part to the excitation detector or to the sample.

6. A fluorometer as defined in claim 5, wherein the means for conducting is a glass plate, semitransparent mirror, a mirror smaller than the area of the excitation channel, or an optical fiber.

7. A fluorometer as defined in claim 1, wherein the excitation polariser includes a first polarisation filter and a second polarisation filter, so that one of the polarisation filters can in turn be placed on the path of light directed from a light source, or wherein the excitation polariser is a rotatable polariser.

8. A method for calibrating a polarisation fluorometer, the fluorometer including an excitation channel configured to conduct polarised excitation light to a sample, an emission channel configured to conduct emission light from the sample, and a reference detector, the emission channel including a polarisation filter, the method comprising:

placing a first polarisation filter in the excitation channel, wherein light is conducted through the excitation channel and intensity of the transmitted light is measured by an excitation detector;

then, removing the first polarisation filter and replacing with a second polarisation filter having a polarisation plane inversed relative to the polarisation plane of the first polarisation filter, wherein light is conducted through the excitation channel, and intensity of the transmitted light is measured by the excitation detector, wherein a part of the polarised light of the excitation channel is conducted to the reference detector and a part to the excitation detector; and based on the two intensity measurements, calibrating the reference detector to measure accurately sensitivities of the fluorometer on the polarisation planes.

9. A method as defined in claim 8, wherein the second polarisation filter is inversed 90 degrees relative to the first polarisation filter.

10. A method as defined in claim 8, wherein the intensities are measured without any sample.

11. A method as defined in claim 8, wherein the intensities are measured without any sample vessel provided in the fluorometer.

12. A method for measuring polarisation fluorescence spectrum of a sample, in which method the polarisation of the sample is measured at different wavelengths by a fluorometer as defined in claim 1.

13. A method for measuring polarisation fluorescence spectrum of a sample, in which method the polarisation of the sample is measured at different wavelengths by a fluorometer calibrated as defined in claim 8.

14. A fluorometer as defined in claim 1, wherein the emission channel does not include a reference detector.

* * * * *